(12) United States Patent
Jiang et al.

(10) Patent No.: US 8,535,482 B2
(45) Date of Patent: Sep. 17, 2013

(54) DRY FLUFF PULP SHEET ADDITIVE

(75) Inventors: Jianer Jiang, Mason, OH (US); James E. Sealey, Loveland, OH (US)

(73) Assignee: International Paper Company, Memphis, TN (US)

( * ) Notice: Subject to any disclaimer, the term of this patent is extended or adjusted under 35 U.S.C. 154(b) by 31 days.

(21) Appl. No.: 12/851,121

(22) Filed: Aug. 5, 2010

(65) Prior Publication Data

US 2011/0034891 A1 Feb. 10, 2011

Related U.S. Application Data

(60) Provisional application No. 61/231,399, filed on Aug. 5, 2009.

(51) Int. Cl.
*D21H 11/00* (2006.01)

(52) U.S. Cl.
USPC ...................................................... 162/164.1

(58) Field of Classification Search
USPC ................. 162/164.1, 158, 173, 179, 181.9; 604/358; 428/219, 220
See application file for complete search history.

(56) References Cited

U.S. PATENT DOCUMENTS

| | | |
|---|---|---|
| 3,395,708 A | 8/1968 | Hervey et al. |
| 3,554,862 A | 1/1971 | Hervey et al. |
| 3,627,630 A | 12/1971 | Gagnon |
| 3,819,470 A | 6/1974 | Shaw et al. |
| 3,903,889 A | 9/1975 | Torr |
| 4,022,965 A | 5/1977 | Goheen et al. |
| 4,075,136 A | 2/1978 | Schaper |
| 4,081,316 A | 3/1978 | Aberg et al. |
| 4,089,647 A | 5/1978 | Mockli |
| 4,166,894 A | 9/1979 | Schaper |
| 4,174,417 A | 11/1979 | Rydell |
| 4,383,834 A | 5/1983 | Degen et al. |
| 4,394,212 A | 7/1983 | Pociluyko |
| 4,425,186 A | 1/1984 | May et al. |
| 4,431,481 A | 2/1984 | Drach et al. |
| 4,439,271 A | 3/1984 | Samuelson |
| 4,496,427 A | 1/1985 | Davison |
| 4,720,383 A | 1/1988 | Drach et al. |
| 4,777,736 A | 10/1988 | VanOursouw et al. |
| 4,973,382 A | 11/1990 | Kinn et al. |
| 4,986,882 A | 1/1991 | Mackey et al. |
| 5,049,235 A | 9/1991 | Barcus et al. |
| 5,061,344 A | 10/1991 | Wedin et al. |
| 5,068,009 A | 11/1991 | Jokinen et al. |
| 5,160,789 A | 11/1992 | Barcus et al. |
| 5,209,953 A | 5/1993 | Grupe et al. |
| 5,225,047 A | 7/1993 | Graef et al. |
| 5,231,122 A | 7/1993 | Palumbo et al. |
| 5,266,250 A | 11/1993 | Kroyer |
| 5,350,370 A | 9/1994 | Jackson et al. |
| 5,360,420 A | 11/1994 | Cook et al. |
| 5,443,899 A | 8/1995 | Barcus et al. |
| 5,447,603 A | 9/1995 | Michalowski et al. |
| 5,492,759 A | 2/1996 | Eriksson et al. |
| 5,496,626 A | 3/1996 | Hamajima et al. |
| 5,516,569 A | 5/1996 | Veith et al. |
| 5,531,728 A | 7/1996 | Lash |
| 5,601,921 A | 2/1997 | Eriksson |
| 5,662,773 A | 9/1997 | Frederick et al. |
| 5,667,637 A | 9/1997 | Jewell et al. |
| 5,698,074 A | 12/1997 | Barcus et al. |
| 5,698,688 A | 12/1997 | Smith et al. |
| H1704 H | 1/1998 | Wallajapet et al. |
| 5,720,737 A | 2/1998 | Hamajima et al. |
| 5,731,080 A | 3/1998 | Cousin et al. |
| 5,780,616 A | 7/1998 | Fornasari et al. |
| 5,851,672 A | 12/1998 | Wang et al. |
| 5,865,822 A | 2/1999 | Hamajima et al. |
| 6,020,278 A | 2/2000 | Gatenholm |
| 6,059,924 A | 5/2000 | Hoskins |
| 6,074,524 A | 6/2000 | Wu et al. |
| 6,086,950 A | 7/2000 | Masaki et al. |
| H1909 H | 11/2000 | Ahr |
| 6,146,494 A | 11/2000 | Seger et al. |
| 6,153,003 A | 11/2000 | Lee et al. |
| 6,159,335 A | 12/2000 | Owens et al. |
| 6,162,329 A | 12/2000 | Vinson et al. |
| 6,228,223 B1 | 5/2001 | Thebrin et al. |
| 6,248,879 B1 | 6/2001 | Anderson et al. |
| 6,296,737 B1 | 10/2001 | Wu et al. |

(Continued)

FOREIGN PATENT DOCUMENTS

| | | |
|---|---|---|
| CN | 101575820 | 11/2009 |
| EP | 0132128 | 7/1984 |

(Continued)

OTHER PUBLICATIONS

Air Floatation Drying, product sheet, Global Technologies, LLC,[online, 2008, retrieved from the Internet, Retrieved Oct. 30, 2012, URL, http.www.globaltechllc.com-airfloat.html.

(Continued)

*Primary Examiner* — Mark Halpern
(74) *Attorney, Agent, or Firm* — Thomas W. Barnes, II; John K. Pike (57) ABSTRACT

A process is provided for making a fluff pulp sheet, comprising forming a web comprising fluff pulp fibers; and applying at least one debonder surfactant to the web, to make the fluff pulp sheet. A fluff pulp sheet is also provided, comprising a web comprising fluff pulp fibers; at least one debonder surfactant; and a fiberization energy of <145 kJ/kg. Products and uses of the fluff pulp sheet are also provided.

16 Claims, 1 Drawing Sheet

(56) References Cited

U.S. PATENT DOCUMENTS

| | | |
|---|---|---|
| 6,340,408 B1 | 1/2002 | Norlander |
| 6,361,651 B1 | 3/2002 | Sun |
| 6,417,425 B1 | 7/2002 | Whitmore et al. |
| 6,419,790 B1 | 7/2002 | Leege et al. |
| 6,458,343 B1 | 10/2002 | Zeman et al. |
| 6,471,824 B1 | 10/2002 | Jewell |
| 6,506,282 B2 | 1/2003 | Hu et al. |
| 6,533,898 B2 | 3/2003 | Gross |
| 6,579,414 B2 | 6/2003 | Jewell |
| 6,579,415 B2 | 6/2003 | Jewell |
| 6,582,557 B2 | 6/2003 | Jewell |
| 6,592,712 B2 | 7/2003 | Koukoulas et al. |
| 6,592,717 B2 | 7/2003 | Jewell |
| 6,603,054 B2 | 8/2003 | Chen et al. |
| 6,667,424 B1 | 12/2003 | Hamilton et al. |
| 6,692,603 B1 | 2/2004 | Lindsay et al. |
| 6,770,576 B2 | 8/2004 | Cook et al. |
| 6,808,790 B2 | 10/2004 | Chen et al. |
| 6,811,879 B2 | 11/2004 | Dezutter et al. |
| 6,837,970 B2 | 1/2005 | Ko et al. |
| 6,893,473 B2 | 5/2005 | Neogi et al. |
| 6,918,992 B1 | 7/2005 | Strandberg et al. |
| 6,930,221 B1 | 8/2005 | Strandqvist |
| 7,175,741 B2 | 2/2007 | West et al. |
| 7,265,258 B2 | 9/2007 | Hamilton et al. |
| 7,334,347 B2 | 2/2008 | Mann et al. |
| 7,344,593 B2 | 3/2008 | Luo et al. |
| 7,442,279 B2 | 10/2008 | Hermans et al. |
| 7,479,578 B2 | 1/2009 | Garnier et al. |
| 7,592,391 B2 | 9/2009 | Calhoun et al. |
| 2002/0096276 A1 | 7/2002 | Leithem et al. |
| 2002/0099347 A1 | 7/2002 | Chen et al. |
| 2003/0034137 A1 | 2/2003 | Neogi et al. |
| 2003/0139716 A1 | 7/2003 | Falk |
| 2004/0122389 A1 | 6/2004 | Mace et al. |
| 2004/0123483 A1 | 7/2004 | Vrbanac et al. |
| 2005/0137547 A1 | 6/2005 | Didier Garnier et al. |
| 2006/0137838 A1 | 6/2006 | Luo et al. |
| 2006/0137842 A1 | 6/2006 | Garnier et al. |
| 2006/0173432 A1 | 8/2006 | Laumer et al. |
| 2006/0184147 A1 | 8/2006 | Hamed |
| 2006/0246186 A1 | 11/2006 | Nowak et al. |
| 2006/0260773 A1 | 11/2006 | Tan et al. |
| 2007/0083018 A1 | 4/2007 | Liu et al. |
| 2007/0218256 A1 | 9/2007 | Tani |
| 2007/0277947 A1 | 12/2007 | Nguyen |
| 2008/0082069 A1 | 4/2008 | Qin et al. |
| 2009/0124989 A1 | 5/2009 | Wastlund-Karlsson et al. |
| 2010/0311296 A1 | 12/2010 | Boehmer et al. |
| 2011/0030908 A1 | 2/2011 | Sealey et al. |
| 2011/0108227 A1 | 5/2011 | Sealey et al. |
| 2012/0017808 A1 | 1/2012 | Sealey et al. |
| 2012/0048493 A1 | 3/2012 | Sealey |

FOREIGN PATENT DOCUMENTS

| | | |
|---|---|---|
| EP | 0225940 | 12/1985 |
| EP | 184603 | 6/1986 |
| EP | 399564 | 11/1990 |
| EP | 896045 | 2/1999 |
| EP | 1217120 | 6/2002 |
| EP | 1548165 | 6/2005 |
| GB | 301682 | 12/1928 |
| GB | 868651 | 5/1961 |
| GB | 1180801 | 2/1970 |
| GB | 1367670 | 9/1974 |
| GB | 1489520 | 10/1977 |
| GB | 1550880 | 8/1979 |
| WO | 8902952 | 4/1989 |
| WO | 9000213 | 1/1990 |
| WO | 9105106 | 4/1991 |
| WO | 9412725 | 6/1994 |
| WO | 9602697 | 2/1996 |
| WO | 9722744 | 6/1997 |
| WO | 2006060221 | 6/2006 |
| WO | 2006119392 | 11/2006 |
| WO | 2007027966 | 3/2007 |
| WO | 2008058563 | 5/2008 |
| WO | 2011017532 | 2/2011 |
| WO | 2011017541 | 2/2011 |

OTHER PUBLICATIONS

Smook, Gary A., Handbook of Pulp and Paper Terminology, Angus Wilde Publications, 1990, pp. 51.

Smook, Gary A., Handbook of Pulp and Paper Terminology, Angus Wilde Publications, 1990, p. 85.the definition of fluff pulp.

DRY FLUFF PULP SHEET ADDITIVE

BACKGROUND

Field of the Invention

The invention relates to fluff pulp sheets, processes for making, and their use.

BRIEF DESCRIPTION OF THE FIGURES

Various embodiments are described in conjunction with the accompanying figures, in which.

DETAILED DESCRIPTION OF THE SEVERAL EMBODIMENTS

One embodiment of the subject matter claimed herein results in significantly reduced operational risk, e.g., sheet breaking, in the manufacture of fluff pulp sheets. Another embodiment of the subject matter claimed herein results in improved fluff shred quality of fluff pulp sheets. Another embodiment of the subject matter claimed herein results in improved fluff fiber singulation of fluff pulp sheets. Another embodiment of the subject matter claimed herein results in reduced fiberization energy of fluff pulp sheets. Another embodiment of the subject matter claimed herein results in good Mullen values of fluff pulp sheets. Another embodiment of the subject matter claimed herein results in a fluff pulp sheet with reduced fiberization energy but which maintains good Mullen value. Another embodiment of the subject matter claimed herein is a fluff pulp sheet having improved surfactant retention. Another embodiment of the subject matter claimed herein is a fluff pulp sheet or absorbent product obtained therefrom having improved absorbency and low absorption times. In one embodiment, the fluff pulp sheet can be processed at high speeds without sheet breaks or other processing issues. In another embodiment, the subject matter claimed herein avoids the disadvantages of conveying a mechanically weak sheet through a paper machine.

One embodiment of the invention relates to a process for making a fluff pulp sheet, comprising:
   forming a web comprising fluff pulp fibers; and
   applying at least one debonder surfactant to the web, to make the fluff pulp sheet.

In one embodiment, the forming comprises one or more of contacting a fluff pulp mixture comprising fluff pulp fibers and water with a table in a papermaking machine, removing at least a portion of water from a fluff pulp mixture comprising fluff pulp fibers and water with a suction box under a table in a papermaking machine, at least partially drying a fluff pulp mixture comprising fluff pulp fibers and water in a flotation dryer, heating a fluff pulp mixture comprising fluff pulp fibers and water, heating the debonder surfactant, or a combination thereof.

The debonder surfactant may be suitably applied to the web. For example, the debonder surfactant may be suitably sprayed onto the web using a formation shower or spray boom over the table, coated onto the web using known coating methods in the papermaking arts, or the web may be immersed into the debonder surfactant. Combinations of application methods are possible.

In one embodiment, the debonder surfactant is sprayed onto the web.

In one embodiment, the spraying is carried out using one or more formation showers over a table in a papermaking machine.

In embodiment, the web may be dried in a dryer, to form a dried web or fluff pulp sheet. The web may be suitably dried in a drying section. Any method for drying commonly known in the art of fluff pulp papermaking may be utilized. The drying section may include and contain a drying can, flotation dryer, cylinder drying, Condebelt drying, IR, or other drying means and mechanisms known in the art. The fluff pulp sheet may be dried so as to contain any selected amount of water. In one embodiment, the web is dried using a flotation dryer.

In one embodiment, the applying comprises applying the debonder surfactant to the dried web.

In another embodiment, a debonder surfactant may further and optionally be applied to the fluff pulp sheet. The thus-applied second debonder surfactant may be the same or different from the debonder surfactant applied to the web. In one embodiment, the second debonder surfactant is applied to the fluff pulp sheet after the last drying step. In one embodiment the second debonder surfactant is applied to the fluff pulp sheet before the sheet is taken up on the reel. The second debonder surfactant may be suitably applied by spraying, for example, from a second formation shower or spray boom located at the dry end.

The web may be suitably dried to a moisture content of between 0 and 70%. This range includes all values and subranges therebetween, including 0, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25, 30, 35, 40, 45, 50, 55, 60, 65, 70% or any combination thereof or range therein. In one embodiment, the web is dried to a moisture content of $\leq 70\%$. In another embodiment, the web is dried to a moisture content of $\leq 50\%$. In another embodiment, the web is dried to a moisture content of $\leq 25\%$. In another embodiment, the web is dried to a moisture content of $\leq 10\%$. In another embodiment, the web is dried to a moisture content of $\leq 7\%$. In another embodiment, the web is dried to a moisture content of about 6.3%.

In one embodiment, the web may have a basis weight ranging from 100 to 1100 gsm. This range includes all values and subranges therein, for example 100, 125, 150, 175, 200, 225, 250, 275, 300, 400, 500, 600, 700, 800, 900, 1000, 1100, or any combination thereof or range therein.

In one embodiment, the solids content of the web and/or fluff pulp sheet at the point or points of applying the debonder surfactant may suitably range from 1 to 100%. This range includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 99, 100%, or any combination thereof or any range therein. In one embodiment, the solids content of the web and/or fluff pulp sheet at the point or points of applying one or more debonder surfactant is >1%. In another embodiment, the solids content of the web and/or fluff pulp sheet at the point or points of applying one or more debonder surfactant is >25%. In another embodiment, the solids content of the web and/or fluff pulp sheet at the point or points of applying one or more debonder surfactant is >50%.

In one embodiment, the fluff pulp mixture further comprises one or more additive such as whitener, colorant, pigment, optical brightening agent, wetting agent, binder, bleaching agent, other additive, or a combination thereof. If present, the amount of additive is not particularly limited. In one embodiment, the additive may be present in amounts ranging from about 0.005 to about 50 weight percent based on the weight of the fluff pulp mixture. This range includes all values and subranges therebetween, including about 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, and 50 weight percent, or any combination thereof, based on the weight of the fluff pulp mixture.

In one embodiment, the web comprises a solids content of >1% by weight. This range includes all values and subranges therein, including 100, 99, 98, 97, 96, 95, 94, 93, 92, 91, 90, 85, 80, 75, 70, 65, 60, 55, 50, 45, 40, 35, 30, 25, 20, 15, 10, 9, 8, 7, 6, 5, 4, 3, 2, >1%, or any combination thereof or range therein.

In one embodiment, the debonder surfactant is applied neat or as purchased. In another embodiment, the debonder surfactant is used in combination with one or more second debonder surfactant. In another embodiment, the debonder surfactant is applied from a solution, dispersion, emulsion, or the like. If applied in solution, dispersion, emulsion, or the like, or combination thereof. In one embodiment, if applied in solution, dispersion, emulsion, or the like, the debonder surfactant concentration may suitably range from 1 to 50% by weight solids content of debonder surfactant to the weight of solution, dispersion, emulsion, or the like. This range includes all values and subranges therebetween, including 0.5, 1, 2, 3, 4, 5, 6, 7, 8, 9, 10, 11, 12, 13, 14, 15, 16, 17, 18, 19, 20, 25, 30, 35, 40, 45, 50%, or any combination thereof or range therein.

In one embodiment, the debonder surfactant is in the form of a composition further comprising water and optionally one or more pH adjusting agent, whitener, colorant, pigment, optical brightening agent, wetting agent, binder, bleaching agent, trivalent cationic metal, alum, other additive, or a combination thereof. If present, the amount of additive is not particularly limited. In one embodiment, the additive may be present in amounts ranging from about 0.005 to about 50 weight percent based on the weight of the debonder surfactant composition. This range includes all values and subranges therebetween, including about 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, and 50 weight percent, or any combination thereof, based on the weight of the debonder surfactant composition.

Debonder surfactants are known in the fluff pulp and fluff pulp fiber arts. Any debonder surfactant is suitable for use in the present application, and the selection thereof is within the skill of one knowledgeable in the fluff pulp and fluff pulp fiber arts. Some examples, which are not intended to be limiting, include linear or branched monoalkyl amine, linear or branched dialkyl amine, linear or branched tertiary alkyl amine, linear or branched quaternary alkyl amine, ethoxylated alcohol, linear or branched, saturated or unsaturated hydrocarbon surfactant, fatty acid amide, fatty acid amide quaternary ammonium salt, dialkyl dimethyl quaternary ammonium salt, dialkylimidazolinium quaternary ammonium salt, dialkyl ester quaternary ammonium salt, triethanolamine-ditallow fatty acid, fatty acid ester of ethoxylated primary amine, ethoxylated quaternary ammonium salt, dialkyl amide of fatty acid, dialkyl amide of fatty acid, cationic surfactant, non-ionic surfactant, $C_{16}$-$C_{18}$ unsaturated alkyl alcohol ethoxylate, commercially available compound having CAS Registry No. 68155-01-1, commercially available compound having CAS Registry No. 26316-40-5, commercially available F60™, commercially available Cartaflex TS LIQ™, commercially available F639™, commercially available Hercules PS9456™, commercially available Cellulose Solutions 840™, commercially available Cellulose Solutions 1009™, commercially available EKA 509H™, commercially available EKA 639™, alone, or in any combination. Other examples of debonder surfactants are disclosed in U.S. Pat. No. 4,425,186, the contents of which being hereby incorporated by reference.

Given the teachings herein, and the knowledge of one skilled in the fluff pulp papermaking arts, one can easily determine the method of applying the debonder surfactant to the web, and the amount, composition, temperature, residence time, and the like, to carry out the subject matter claimed herein. For example, the total amount of debonder surfactant in the web and/or in the finished fluff pulp sheet may be increased or decreased or otherwise controlled by controlling the various points of addition. For example, the amount of debonder surfactant applied at the wet end may be increased or decreased by respectively decreasing or increasing that amount applied at the dry end. Further one or more than one of the same or different type of debonder surfactant, or any combination thereof, may be applied at any point in the process.

In another embodiment, the web further comprises water and optionally one or more debonder surfactant, pH adjusting agent, whitener, colorant, pigment, optical brightening agent, wetting agent, binder, bleaching agent, trivalent cationic metal, alum, other additive, or a combination thereof.

In one embodiment, the finished fluff pulp sheet may be fiberized or shredded, in accordance with methods known in the art. For example, the fiberizing or shredding may be carried out in a hammermill.

In one embodiment, the fluff pulp sheet and/or fiberized or shredded fluff pulp sheet, or a combination thereof may be suitably incorporated into one or more of an adsorbent product, paper product, personal care product, medical product, insulating product, construction product, structural material, cement, food product, veterinary product, packaging product, diaper, tampon, sanitary napkin, gauze, bandage, fire retardant, or a combination thereof. These products and methods for their manufacture and use are well known to those of ordinary skill in the art.

Another embodiment relates to a fluff pulp sheet, made by the process described herein.

Another embodiment relates to a fluff pulp sheet, comprising:
 a web comprising fluff pulp fibers;
 at least one debonder surfactant; and
 a fiberization energy of <145 kJ/kg.

The fiberization energy, sometimes called the shred energy, of the fluff pulp sheet is suitably less than 145 kJ/kg. This range includes all values and subranges therebetween, including 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145 kJ/kg, or any combination thereof or any range therein. In one embodiment, the fiberization energy of the fluff pulp sheet is less than 135 kJ/kg. In another embodiment, the fiberization energy of the fluff pulp sheet is from 120 to less than 145 kJ/kg. In another embodiment, the fiberization energy of the fluff pulp sheet is less than 120 kJ/kg. In another embodiment, the fiberization energy of the fluff pulp sheet is from 100 to 120 kJ/kg. In another embodiment, the fiberization energy of the fluff pulp sheet is less than 100 kJ/kg. In another embodiment, the fiberization energy of the fluff pulp sheet is less than 95 kJ/kg.

In one embodiment, the fluff pulp sheet has a SCAN-C 33:80 adsorption time of <4.0 s. This range includes all values and subranges therebetween, including 1, 1.1, 1.2, 1.3, 1.4, 1.5, 1.6, 1.7, 1.8, 1.9, 2, 2.0, 2.1, 2.2, 2.3, 2.4, 2.5, 2.6, 2.7, 2.8, 2.9, 3, 3.0, 3.1, 3.2, 3.3, 3.4, 3.5, 3.6, 3.7, 3.8, 3.9, <4.0 s, or any range therein.

In one embodiment, the fluff pulp sheet on screen fractionation has a % Good of ≧50%. This range includes all values and subranges therebetween, including 50, 55, 60, 65, 70, 75, 80, 85, 90, 95, 100%, or any range therein.

In one embodiment, the fluff pulp sheet on screen fractionation has a % Fines of ≦40%. This range includes all values and subranges therebetween, including 1, 2, 3, 4, 5, 6, 7, 8, 9, 10, 15, 20, 25, 30, 35, 40%, or any combination thereof or any range therein.

In one embodiment, the fluff pulp sheet on screen fractionation has a % Pieces of ≦30%. This range includes all values and subranges therebetween, including 1, 2, 3, 4, 5, 6, 7, 8, 9, 10, 15, 20, 25, 30%, or any combination thereof or any range therein.

In one embodiment, the fluff pulp sheet has a Mullen of ≧90 psi. This range includes all values and subranges therebetween, including 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250 psi, and higher, or any range therein.

In one embodiment, the fluff pulp sheet contains the debonder surfactant in an amount of ≧1 lb solids debonder surfactant per ton of the fluff pulp fibers. This range includes all values and subranges therebetween, including 1, 1.1, 1.2, 1.3, 1.4, 1.5, 1.6, 1.7, 1.8, 1.9, 2, 2.0, 2.1, 2.2, 2.3, 2.4, 2.5, 2.6, 2.7, 2.8, 2.9, 3, 3.0, 3.1, 3.2, 3.3, 3.4, 3.5, 3.6, 3.7, 3.8, 3.9, 4, 4.0, 5, 5.0, 6, 7, 8, 9, 10, 15, 20 lb solids debonder surfactant per ton of the fluff pulp fibers, and higher, or any combination thereof or any range therein. In one embodiment, if more than one debonder surfactant is used, this range is the total amount over all the debonder surfactants present in the fluff pulp sheet.

In one embodiment, the fluff pulp sheet has a moisture content of 25% or less. This range includes all values and subranges therebetween, including 0, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 25%, or any combination thereof or range therein. In another embodiment, the fluff pulp sheet has a moisture content of 20% or less. In another embodiment, the fluff pulp sheet has a moisture content of 10% or less. In another embodiment, the fluff pulp sheet has a moisture content of 7% or less. In another embodiment, the fluff pulp sheet has a moisture content of about 6.3%.

In one embodiment, the fluff pulp sheet has a density of 0.5 to 0.75 g/cc. This range includes all values and subranges therebetween, including 0.5, 0.55, 0.6, 0.65, 0.7, and 0.75 g/cc, or any range therein.

In one embodiment, the fluff pulp sheet has a caliper of 40 to 70 mm. This range includes all values and subranges therebetween, including 40, 45, 50, 55, 60, 65, 70 mm, and any range therein.

In one embodiment, the fluff pulp sheet may have a basis weight ranging from 100 to 1100 gsm. This range includes all values and subranges therein, for example 100, 125, 150, 175, 200, 225, 250, 275, 300, 400, 500, 600, 700, 800, 900, 1000, 1100, or any combination thereof or range therein.

Another embodiment relates to an adsorbent product, paper product, personal care product, medical product, insulating product, construction product, structural material, cement, food product, veterinary product, packaging product, diaper, tampon, sanitary napkin, gauze, bandage, fire retardant, or a combination thereof, comprising the fluff pulp sheet and/or fiberized or shredded fluff pulp sheet, or a combination thereof.

Another embodiment relates to the use of an adsorbent product, paper product, personal care product, medical product, insulating product, construction product, structural material, cement, food product, veterinary product, packaging product, diaper, tampon, sanitary napkin, gauze, bandage, fire retardant, or a combination thereof, comprising the fluff pulp sheet and/or fiberized or shredded fluff pulp sheet, or a combination thereof.

Fluff pulp and fluff pulp fibers are known in the papermaking art. Any fluff pulp or fluff pulp fiber is suitable for use in the present application, and the selection thereof is within the skill of one knowledgeable in the fluff pulp and fluff pulp fiber arts. One or more than one, or any combination thereof, of fluff pulp and/or fluff pulp fibers may be used. The fluff pulp and fluff pulp fibers may be treated or untreated, and they may optionally contain one or more than one additives, or combination thereof, which are known in the art. Given the teachings herein, the level of treatment, if desired, and the amount of additives may be readily determined by one of ordinary skill in the fluff pulp and fluff pulp fiber arts.

Similarly, the formation of a web of fluff pulp or fluff pulp fibers or from a fluff pulp mixture or furnish onto a table from a headbox in a papermaking machine is within the skill of one knowledgeable in the fluff pulp and fluff pulp fiber arts.

The type of fluff pulp or fluff pulp fiber suitable for use herein is not intended to be limiting. Fluff pulp typically includes cellulosic fiber. The type of cellulosic fiber is not critical, and any such fiber known or suitable for use in fluff pulp paper can be used. For example, the fluff pulp can made from pulp fibers derived from hardwood trees, softwood trees, or a combination of hardwood and softwood trees. The fluff pulp fibers may be prepared by one or more known or suitable digestion, refining, and/or bleaching operations such as, for example, known mechanical, thermomechanical, chemical and/or semichemical pulping and/or other well known pulping processes. The term, "hardwood pulps" as may be used herein include fibrous pulp derived from the woody substance of deciduous trees (angiosperms) such as birch, oak, beech, maple, and eucalyptus. The term, "softwood pulps" as may be used herein include fibrous pulps derived from the woody substance of coniferous trees (gymnosperms) such as varieties of fir, spruce, and pine, as for example loblolly pine, slash pine, Colorado spruce, balsam fir and Douglas fir. In some embodiments, at least a portion of the pulp fibers may be provided from non-woody herbaceous plants including, but not limited to, kenaf, hemp, jute, flax, sisal, or abaca, although legal restrictions and other considerations may make the utilization of hemp and other fiber sources impractical or impossible. Either bleached or unbleached fluff pulp fiber may be utilized. Recycled fluff pulp fibers are also suitable for use.

The fluff pulp sheet may suitably contain from 1 to 99 wt % of fluff pulp fibers based upon the total weight of the fluff pulp sheet. In one embodiment, the fluff pulp sheet may contain from 5 to 95 wt % of fluff pulp fibers based upon the total weight of the fluff pulp sheet. These ranges include any and all values and subranges therebetween, for example, 1, 5, 10, 15, 20, 25, 30, 35, 40, 45, 50, 55, 60, 65, 70, 75, 80, 85, 90, 95 and 99 wt %.

The fluff pulp sheet may optionally contain from 1 to 100 wt % fluff pulp fibers originating from softwood species based upon the total amount of fluff pulp fibers in the fluff pulp sheet. In one embodiment, the fluff pulp sheet may contain 10 to 60 wt % fluff pulp fibers originating from softwood species based upon the total amount of fluff pulp fibers in the fluff pulp sheet. These ranges include 1, 2, 5, 10, 15, 20, 25, 30, 35, 40, 45, 50, 55, 60, 65, 70, 75, 80, 85, 90, 95, and 100 wt % and any and all ranges and subranges therein, based upon the total amount of fluff pulp fibers in the fluff pulp sheet.

All or part of the softwood fibers may optionally originate from softwood species having a Canadian Standard Freeness (CSF) of from 300 to 750. In one embodiment, the fluff pulp sheet contains fluff pulp fibers from a softwood species having a CSF from 400 to 550. These ranges include any and all values and subranges therebetween, for example, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, and 750 CSF. Canadian Standard Freeness is as measured by TAPPI T-227 standard test.

The fluff pulp sheet may optionally contain from 1 to 100 wt % fluff pulp fibers originating from hardwood species based upon the total amount of fluff pulp fibers in the fluff pulp sheet. In one embodiment, the fluff pulp sheet may contain from 30 to 90 wt % fluff pulp fibers originating from hardwood species, based upon the total amount of fluff pulp fibers in the fluff pulp sheet. These ranges include 1, 2, 5, 10, 15, 20, 25, 30, 35, 40, 45, 50, 55, 60, 65, 70, 75, 80, 85, 90, 95, and 100 wt %, and any and all values and subranges therein, based upon the total amount of fluff pulp fibers in the fluff pulp sheet.

All or part of the hardwood fibers may optionally originate from hardwood species having a Canadian Standard Freeness of from 300 to 750. In one embodiment, the fluff pulp sheet may contain fibers from hardwood species having CSF values of from 400 to 550. These ranges include 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, and 750 CSF, and any and all ranges and subranges therein.

The fluff pulp sheet may optionally contain less refined fluff pulp fibers, for example, less refined softwood fibers, less refined hardwood, or both. Combinations of less refined and more refined fibers are possible. In one embodiment, the fluff pulp sheet contains fibers that are at least 2% less refined than that of fluff pulp fibers used in conventional fluff pulp sheets. This range includes all values and subranges therebetween, including at least 2, 5, 10, 15, and 20%. For example, if a conventional fluff pulp sheet contains fibers, softwood and/or hardwood, having a Canadian Standard Freeness of 350, then, in one embodiment, the fluff pulp sheet may contain fibers having a CSF of 385 (i.e. refined 10% less than conventional).

When the fluff pulp sheet contains both hardwood fluff pulp fibers and softwood fluff pulp fibers, the hardwood/softwood fluff pulp fiber weight ratio may optionally range from 0.001 to 1000. In one embodiment, the hardwood/softwood ratio may range from 90/10 to 30/60. These ranges include all values and subranges therebetween, including 0.001, 0.002, 0.005, 0.01, 0.02, 0.05, 0.1, 0.2, 0.5, 1, 2, 5, 10, 15, 20, 25, 30, 35, 40, 45, 50, 55, 60, 65, 70, 75, 80, 85, 90, 95, 100, 200, 300, 400, 500, 600, 700, 800, 900, and 1000.

The softwood fibers, hardwood fibers, or both may be optionally modified by physical and/or chemical processes to obtain the fluff pulp. Examples of physical processes include, but are not limited to, electromagnetic and mechanical processes. Examples of electrical modifications include, but are not limited to, processes involving contacting the fibers with an electromagnetic energy source such as light and/or electrical current. Examples of mechanical modifications include, but are not limited to, processes involving contacting an inanimate object with the fibers. Examples of such inanimate objects include those with sharp and/or dull edges. Such processes also involve, for example, cutting, kneading, pounding, impaling, and the like, and combinations thereof.

Nonlimiting examples of chemical modifications include conventional chemical fiber processes such as crosslinking and/or precipitation of complexes thereon. Other examples of suitable modifications of fibers include those found in U.S. Pat. Nos. 6,592,717, 6,592,712, 6,582,557, 6,579,415, 6,579,414, 6,506,282, 6,471,824, 6,361,651, 6,146,494, H1, 704, 5,731,080, 5,698,688, 5,698,074, 5,667,637, 5,662,773, 5,531,728, 5,443,899, 5,360,420, 5,266,250, 5,209,953, 5,160,789, 5,049,235, 4,986,882, 4,496,427, 4,431,481, 4,174,417, 4,166,894, 4,075,136, and 4,022,965, the entire contents of each of which are hereby incorporated, independently, by reference.

Some examples of fluff, which are not intended to be limiting, include those commercially available RW Supersoft™, Supersoft L™, RW Supersoft Plus™, GT Supersoft Plus™, RW Fluff LITE™, RW Fluff 110™, RW Fluff 150™, RW Fluff 160™ GP 4881™, GT Pulp™, RW SSP™, GP 4825™, alone, or in any combination.

As discussed herein, if desired, additives such as pH adjusting agent, whitener, colorant, pigment, optical brightening agent, wetting agent, binder, bleaching agent, trivalent cationic metal, alum, other additive, or a combination thereof may be utilized. Such compounds are known in the art and otherwise commercially available. Given the teachings herein, one of ordinary skill in the fluff pulp and fluff pulp papermaking arts would be able to select and use them as appropriate. If present, the amount of additive is not particularly limited. In one embodiment, the additive may be present in amounts ranging from about 0.005 to about 50 weight percent based on the weight of the fluff pulp sheet. This range includes all values and subranges therebetween, including about 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, and 50 weight percent, or any combination thereof, based on the weight of the finished fluff pulp sheet.

One or more optical brightening agents may be optionally present. Typically, the optical brightening agents are fluorescent dyes or pigments that absorb ultraviolet radiation and reemit it at a higher wavelengths in the visible spectrum (blue), thereby effecting a white, bright appearance to the paper sheet when added to the stock furnish, but any optical brightening agent may be used. Examples of optical brighteners include, but are not limited to azoles, biphenyls, coumarins, furans, stilbenes, ionic brighteners, including anionic, cationic, and anionic (neutral) compounds, such as the Eccobrite™ and Eccowhite™ compounds available from Eastern Color & Chemical Co. (Providence, R.I.); naphthalimides; pyrazenes; substituted (e.g., sulfonated) stilbenes, such as the Leucophor™ range of optical brighteners available from the Clariant Corporation (Muttenz, Switzerland), and Tinopal™ from Ciba Specialty Chemicals (Basel, Switzerland); salts of such compounds including but not limited to alkali metal salts, alkaline earth metal salts, transition metal salts, organic salts and ammonium salts of such brightening agents; and combinations of one or more of the foregoing agents.

Examples of optional fillers include, but are not limited to, clay, calcium carbonate, calcium sulfate hemihydrate, and calcium sulfate dehydrate, chalk, GCC, PCC, and the like.

Examples of optional binders include, but are not limited to, polyvinyl alcohol, Amres (a Kymene type), Bayer Parez, polychloride emulsion, modified starch such as hydroxyethyl starch, starch, polyacrylamide, modified polyacrylamide, polyol, polyol carbonyl adduct, ethanedial/polyol condensate, polyamide, epichlorohydrin, glyoxal, glyoxal urea, ethanedial, aliphatic polyisocyanate, isocyanate, 1,6 hexamethylene diisocyanate, diisocyanate, polyisocyanate, polyester, polyester resin, polyacrylate, polyacrylate resin, acrylate, and methacrylate. Other optional substances include, but are not limited to silicas such as colloids and/or sols. Examples of silicas include, but are not limited to, sodium silicate and/or borosilicates.

The composition may optionally and additionally include one or more pigments. Non-limiting examples of pigments include calcium carbonate, kaolin clay, calcined clay, aluminum trihydrate, titanium dioxide, talc, plastic pigment, ground calcium carbonate, precipitated calcium carbonate, amorphous silica, modified calcium carbonate, modified calcined clay, aluminum silicate, zeolite, aluminum oxide, colloidal silica, colloidal alumina slurry, modified calcium carbonate, modified ground calcium carbonate, modified precipitated calcium carbonate, or a mixture thereof.

In one embodiment, the modified calcium carbonate is modified ground calcium carbonate, modified precipitated calcium carbonate, or a mixture thereof. Here, the term, "modified" is sometimes referred to as "structured". These types of pigments are known to those skilled in the papermaking art.

Figure 1:
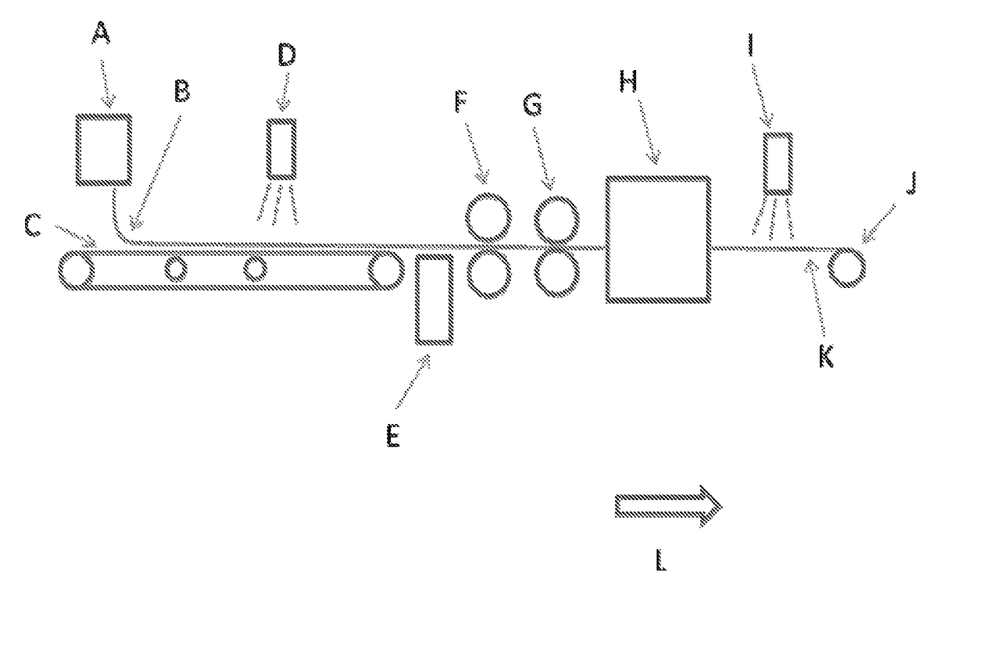
FIG. 1 shows a schematic example of one embodiment of a suitable papermaking machine, wherein A is a head box; B is a composition (e.g., comprising fluff pulp fibers) applied to a table C from head box B; D is a formation shower; E is a suction box; F is a first press; G is a second press or transition to dryer H; I is a formation shower; J is a reel for taking up the finished fluff pulp sheet K; and L is an arrow showing the machine direction of the product as it progresses from head box A to reel J.

The fluff pulp fibers may be formed into a single or multiply web on a papermaking machine such as a Fourdrinier machine or any other suitable papermaking machine known in the art. The basic methodologies involved in making fluff pulp sheets on various papermaking machine configurations are well known to those of ordinary skill in the art and accordingly will not be described in detail herein. In one embodiment, the fluff pulp mixture or fluff pulp fibers may have the form of a relatively low consistency aqueous slurry of the pulp fibers optionally together with one or more additives. In one embodiment, the fluff pulp mixture or fluff pulp fibers slurry is ejected from a head box onto a table, e.g., a porous endless moving forming sheet or wire, where the liquid, e.g., water, is gradually drained through small openings in the wire, optionally with the aid of one or more suction boxes, until a mat of pulp fibers and optionally the other materials is formed on the wire. The debonder surfactant may be applied to the web at any point along the table, for example, by spraying from a formation shower. In one embodiment, the still-wet web is transferred from the wire to a wet press where more fiber-to-fiber consolidation occurs and the moisture is further decreased. In one embodiment, the web is then passed to a dryer section to remove a portion of, most of, or substantially all of the retained moisture and further consolidate the fibers in the web. After drying, the dried web or fluff pulp sheet may be further treated with one or more of the same or different debonder surfactant, or any combination thereof with a formation shower, spray boom, or the like.

The precise location where the respective compositions are applied or contacted may depend on the specific equipment involved, the exact process conditions being used and the like.

These are easily determined given the teachings herein combined with the knowledge of one of ordinary skill in the papermaking art.

EXAMPLES

The claimed subject matter may be described in further detail with reference to the following examples. The examples are intended to be illustrative, but the claimed subject matter is not considered as being limited to the materials, conditions, or process parameters set forth in the examples. All parts and percentages are by unit weight unless otherwise indicated.

The various tests for which results are described herein are provided below:

Fluff Pulp Fiberization Test Procedure or "Johnson Nit" Test:

1. 5.00 g of defibered pulp is placed into the Johnson Nit Counter.
2. Air pressure is set to 100 psi and the test time is set to 600 seconds.
3. At the end of the test the amount retained on the No. 16 screen is weighed and recorded.
4. Then the amount retained on the No. 30 screen is weighed and recorded.
5. The difference between the initial amount and amount retained on the two screens is recorded as the amount passing the No. 30 screen.

Multi-Dose Acquisition Test Procedure:

1. A 5"×12" fluff pulp sample was compressed to a density of 0.154 gms/cm3 using a Beloit Wheeler calendar roll.
2. A sheet of MTS produced coverstock was placed on top of the compressed sample.
3. A 1" diameter dosing tube weighing 1000 g was centered on top of the sample.
4. 30 mls of 0.9% saline solution was dosed at a flow rate of 7 mls/sec.
5. Timing began once the dosage started and ended when all of the saline solution was absorbed and the absorption time was recorded.
6. After 300 seconds after the first dose was absorbed a second dose of saline solution was applied and the timing procedure was repeated and the absorption time recorded.
7. 300 seconds after the second dose was absorbed a third dose was applied and the timing procedure was repeated and the absorption time recorded.

Kamas Mill—Fluff Pulp Shredding:

The Kamas hammermill is a simulation of commercial equipment manufactured and supplied by Kamas Industri AB for use in the production of fluff pulp products. Like the commercial equipment it has variable rotor speed, variable pulp feed speed and exchangeable screens. Pulp strips are hand fed into the mill and are defiberized with free swinging hammers until the resultant fluff is sufficiently broken up to pass through the screen holes.

Fluff Testing Room: Controlled conditions, 72° F. and 55% (+/−5) relative humidity Apparatus: Kamas Type H 01 Laboratory Defribrator Sample Preparation Condition pulp sheets in the testing room for at least 4 hours. For lab test sheets, trim about ½" from edges. Cut pulp sheets into strips, 5-10 strips/sample if available, 2 inches wide. Record weights. Clean dust bag if necessary. Ensure that milling chamber is clean and desired screen is properly inserted. Make sure the collection funnel/screen is securely in place. Set rotor to 3300 rpm, feed to 15 cm/sec and use 10 mm screen unless otherwise specified. Feed pulp strip into mill. The energy will be automatically measured and displayed. Make sure weight entry is correct. Collect the shredded pulp in the collection screen receptor below the shredding chamber—maximum capacity is 4-5 strips. Empty fluff into plastic bag. Mix by hand, then seal bag and shake vigorously to get a homogenous fluff mix.

4 Screen Fractionation of Shredded Fluff Pulp:

Purpose: To determine the size distribution of fibers in dry shredded pulp. A moving high velocity air stream disperses shredded pulp in a covered standard testing sieve while individual fibers are removed through the wire mesh by an applied vacuum. The amount of fluff retained on the sieve wire is determined by weight. The fiber is subjected to fractionation through a series of sieves with consecutively increasing hole openings. The fractions are calculated as a percentage of the original whole fluff weight.

Apparatus: Pulp fluff air turbulence generator and separator

USA Standard Testing Sieves: 8" diameter×2" height.

USA Std #200 (75 um hole opening)

USA Std #50 (300 um hole opening)

USA Std #14 (1400 um hole opening)

USA Std #8 (2360 um hole opening

Notes: This test must be conducted in a controlled room, 48% to 52% relative humidity, 70° F. to 72° F.

Procedure: (1) Condition shredded pulp at least 4 hrs in the test room. Mix the fluff in the plastic bag by hand and by vigorously shaking the sealed bag which contains air space, to achieve as uniform a distribution of fiber fractions as possible, i.e., to achieve a representative test sample. (2) Take pulp from various areas of the bag, and weigh out 5 grams (+/−0.01 grams). Record weight, and place on a tared #200 sieve. Place sieve on the fluff fractionator and cover. Seal the seam formed by the sieve with the large rubber gasket. This allows a more uniform distribution of the air/vacuum. (3) Set timer for 5 minutes and start the fractionator by turning knob to "auto". Adjust the compressed air to 30 psi and the vacuum to 4 inches using the three holed circular plexiglass adjustment device. (Note: Vacuum/air psi may drift, check intermittently). The fines will pass through the sieve into the vacuum. At the end of the set time period, the unit shuts off automatically. When finished, remove the sieve. Remove the cover and weigh the sieve plus the pulp on the tared balance. Record the weight of pulp remaining on the #200 sieve. The mass of the fines is the difference in the mass of the pulp before and after fractionation. (4) Tare the #50 sieve and transfer the pulp from step 3 on to the #50 sieve, cover, place on fractionator and seal as in step 2. Set timer for 5 minutes. Reset the start by turning the knob to off, then back to auto. Start fractionator and proceed as in step 3 (adjust air and vacuum as needed). Record the weight of the pulp retained on the #50 screen. (5) Tare the #14 sieve and transfer the pulp from the #50 on to the #14 sieve, cover, place on fractionator and seal as in step 2. Set timer for 5 minutes. Reset the start by turning the knob to off, then back to auto. Start fractionator and proceed as in step 3 (adjust air and vacuum as needed). Record weight of the pulp retained on the #14 screen. (6) Transfer the pulp from the #14 to the #8 screen. Repeat the process above (5 minutes, 30 psi, vacuum at 4 in.) and record the weight of pulp retained on the #8. Percent passing #200 is reported as Fines. Percent retained on #200 screen, but passing #50 is reported as Good. Percent retained on #50, but passing #14 is reported as Good (Total Good is sum of the two good fractions). Percent retained on #14 screen, but passing #8 screen is reported as Nits (fiber agglomerates). Percent retained on #8 screen is reported as Pieces.

Calculations:

Original fluff weight

Weight remaining on #200

Weight remaining on #50

Weight remaining on #14

Weight remaining on #8

$$\text{Percent passing \#200} = \frac{(1)-(2)}{(1)} \times 100 = \% \text{ Fines}$$

$$\text{Percent retained on \#200} = \frac{(2)-(3)}{(1)} \times 100 = \% \text{ Good}$$

$$\text{Percent retained on \#50} = \frac{(3)-(4)}{(1)} \times 100 = \% \text{ Good}$$

$$\text{Percent retained on \#14} = \frac{(4)-(5)}{(1)} \times 100 = \% \text{ Nits (fiber agglomerates)}$$

$$\text{Percent retained on \#8} = \frac{(5)}{(1)} \times 100 = \% \text{ Pieces}$$

Run a minimum of three tests per sample.

Scan Absorption Test:

Purpose: To determine absorption properties of fluff pulp pads. The method is based on the Scandinavian standard SCAN-C 33:80. Fluff volume (bulk), absorption rate and absorption capacity are measured by placing a test pad on the unit, applying a uniform load and allowing the pad to absorb liquid from below until saturated.

Apparatus: SCAN Absorption Tester consisting of a test piece former, absorption unit and timing device.

Reagents: 0.9% saline (NaCl) solution

Procedure: (1) Prepare saline solution, 0.9% sodium chloride in DI water (e.g., 180 g/20 L) and transfer to saline delivery carboy. (2) Setup: Rinse electrode platen and blot dry with wipe; rinse screen and reservoir to remove residue, dry and replace in tester. Open valve on carboy and run saline through until it flows into overflow pail. Close valve. May need to stabilize the instrument by running a few samples before analyzing test samples. (3) Mix fluff by vigorously shaking inflated sample bag. Weigh out approximately 3.20 g of fluff pulp (take several small portions throughout the bag to get a representative sample). (4) Tare the forming tube (the plexiglass cylindrical mold with 50 mm base screen) and place securely on pad former (make sure it's firmly seated on gasket). Turn on vacuum and carefully feed the pulp into the former in small amounts, allowing fibers to separate as much as possible. Avoid feeding in clumps of pulp. (5) After pad has been formed turn off vacuum and remove mold/screen assembly. Place tared assembly with pad on balance and remove excess pulp to give a final weight of 3.00 g+/−0.01. Arrange pulp as needed to give uniform thickness. Fibers sometimes build up on one side in tube, especially if high in nits. Remove from this area first to get the 3.00 g, then rearrange as needed, carefully lifting mat/fibers to the thinner area. Gently tamp down the moved fibers to give a uniform thickness. Prepare 6-8 pads per sample. (6) Setup computer: Turn computer on. Enter ID and sample wt (i.e., 3.00 g). (7) Pre-wet the SCAN tester sample basket and use wipe to remove excess. Lower the electrode platen and click "Zero" on the computer to zero height sensor. Raise and latch the electrode platen. (8) Remove bottom screen from forming tube. Place plexi tube on the SCAN wire basket; gently lower the electrode platen (with the load on top of shaft) onto the pad, carefully raise the mold (hold in place), click "Start" on computer to start the timer on computer screen, then swing holder over and rest the tube on it. Avoid touching the wires and shaft with the tube. Watch the screen and start the saline flow at about 18-20 seconds. When prompted (at 30 sec), raise the reservoir in one even motion (hold in place) and immediately start manual timer. Watch the pad and stop manual timer as soon as liquid has wicked up. When prompted on the computer screen, carefully lower the reservoir, close the saline valve and allow pad to drain. When prompted "test over", raise the electrode platen up through the former tube. If pad sticks to the platen, gently tap with edge of tube to release pad onto the basket. Latch the electrode platen, remove forming tube and carefully transfer pad to a balance. Record wet weight. Enter wet pad weight in instrument computer. Record the dry height (caliper, m), specific volume (cc/g), absorption time (sec), and absorption capacity as displayed, and the manual time wet weight, on spreadsheet. Report absorption time (sec), absorption rate (cm/sec), specific volume (g/cc), and capacity (g/g). Run 6-10 tests per sample. Report averages and SD.

Example 1

In Samples 719-727, a commercially available debonder surfactant, F60, available from Akzo Nobel, was sprayed onto dried webs comprising fluff pulp fibers in accordance with one or more embodiments of the claimed subject matter. The moisture content of the dried webs was 6.3%. The LA Control and NB 405 samples are provided for comparison, and are commercially available untreated and treated fluff pulp sheets, respectively.

TABLE 1

| Sample | F60 Debonder Surfactant Targeted Dose lbs F60/ton of dry fiber | F60 Debonder Surfactant Solution Concentration % | Fiberization energy kJ/kg | Mullen PSI |
|---|---|---|---|---|
| 719 | 2.5 | 7.5 | 91 | 125 |
| 720 | 3 | 7.5 | 84 | 122 |
| 721 | 3.5 | 7.5 | 77 | 103 |
| 722 | 2.5 | 8.5 | 70 | 122 |
| 723 | 3 | 8.5 | 86 | 136 |
| 724 | 3.5 | 8.5 | 71 | 122 |
| 725 | 2.5 | 9.5 | 77 | 133 |
| 726 | 3 | 9.5 | 90 | 133 |
| 727 | 3.5 | 9.5 | 70 | 128 |
| LA Control | 0 | 0 | 135 | 168 |
| NB 405 | NA | NA | 86 | 83 |

The spray-on application of F60 produces a fluff pulp sheet with a fiberization energy equal to a fully treated fluff pulp (NB 405 as example), but surprisingly the sheet Mullen doesn't drop to a low level. This enables the sheet to remain processable through the winder at high speeds without sheet breaks or processing issues. The spray-on application occurred on a fully dried sheet in this example, 6.3% MC. If desired, the chemical and sheet can both be heated (~160° F.) or room temperature during application. One advantage of adding the debonder to the dry fluff sheet (of 100 to 1100 GSM basis weight) is the issue of conveying a mechanically weak sheet through the paper machine is avoided. Surfactant retention is also improved.

Without wishing to be bound by theory, it is possible that the fact that this spray-on application works because some migration or mixing of the chemical occurs during fiberization. Shred quality or fiber singulation is equal to traditional debonder application methods, but processing difficulties, e.g., sheet breaking, etc., is significantly improved.

F60 will not retain if added to the stock before the headbox. Without wishing to be bound by theory, it is possible that the chemistry required for a surfactant that helps to reduce the energy to separate the fibers during fiberization, but doesn't induce large reduction in absorption rate of fluff core, must be only slightly cationic. The highly polar surfactants retain well on the pulp fiber but they tend to create a fluff core with significantly reduce absorption properties (Re-wet and rate of absorption).

From the results shown in the tables and graphically illustrated in the Figures, it is clear that the examples within the scope of one embodiment of the invention inhere surprising and unexpectedly superior benefits when compared to those comparative examples.

As used throughout, ranges are used as a short hand for describing each and every value that is within the range, including all subranges therein.

All other references, as well as their cited references, cited herein are hereby incorporated by reference with respect to relative portions related to the subject matter of the present invention and all of its embodiments.

Numerous modifications and variations on the present invention are possible in light of the above teachings. It is, therefore, to be understood that within the scope of the accompanying claims, the invention may be practiced otherwise than as specifically described herein.

What is claimed is:

1. A process for making a fluff pulp sheet, comprising:
   forming, on a table of a papermaking machine, a web comprising fluff pulp fibers; and
   spraying at least one debonder surfactant onto the web, wherein said spraying is carried out on the table and prior to a dryer section, to make the fluff pulp sheet;
   wherein the debonder surfactant is one or more selected from the group consisting of linear or branched monoalkyl amine, linear or branched dialkyl amine, linear or branched tertiary alkyl amine, linear or branched quaternary alkyl amine, fatty acid amide, fatty acid amide quaternary ammonium salt, dialkyl dimethyl quaternary ammonium salt, dialkylimidazolinium quaternary ammonium salt, dialkyl ester quaternary ammonium salt, triethanolamine-ditallow fatty acid, dialkyl amide of fatty acid, dialkyl amide of fatty acid, compound having CAS Registry No. 68155-01-1, compound having CAS Registry No. 26316-40-5, and a combination thereof.

2. The process of claim 1, wherein the forming comprises one or more of contacting a fluff pulp mixture comprising fluff pulp fibers and water with the table, removing at least a portion of water from a fluff pulp mixture comprising fluff pulp fibers and water with a suction box under the table, heating a fluff pulp mixture comprising fluff pulp fibers and water, heating the debonder surfactant, or a combination thereof.

3. The process of claim 1, wherein the spraying is carried out using one or more formation showers over the table.

4. The process of claim 1, wherein the web has a basis weight of 100 to 1100 gsm.

5. The process of claim 1, wherein the web further comprises water and optionally one or more debonder surfactant, pH adjusting agent, whitener, colorant, pigment, optical brightening agent, wetting agent, binder, bleaching agent, trivalent cationic metal, alum, other additive, or a combination thereof.

6. The process of claim 1, wherein the web comprises a solids content of >1% by weight.

7. The process of claim 1, wherein the debonder surfactant is neat, in combination with one or more second debonder surfactant, in solution, or combination thereof.

8. The process of claim 1, wherein the debonder surfactant is in the form of a composition further comprising water and optionally one or more pH adjusting agent, whitener, colorant, pigment, optical brightening agent, wetting agent, binder, bleaching agent, trivalent cationic metal, alum, other additive, or a combination thereof.

9. The process of claim 1, further comprising fiberizing or shredding the fluff pulp sheet.

10. The process of claim 9, wherein the fiberizing or shredding are carried out in a hammermill.

11. The process of claim 1, further comprising incorporating the fluff pulp sheet into one or more of an adsorbent product, paper product, personal care product, medical product, insulating product, construction product, structural material, cement, food product, veterinary product, packaging product, diaper, tampon, sanitary napkin, gauze, bandage, fire retardant or a combination thereof.

12. The process of claim 1, wherein the debonder surfactant is applied as a solution, dispersion, or emulsion at a concentration of 1 to 50% by weight solids content of debonder surfactant to the weight of the solution, dispersion, or emulsion.

13. The process of claim 1, further comprising spraying a second debonder surfactant onto the fluff pulp sheet.

14. The process of claim 1, further comprising, after the spraying, drying the web to a moisture content of between 0 and 70%.

15. The process of claim 1, wherein the debonder surfactant is present in an amount of 1 to 20 lbs per ton of fluff pulp fibers.

16. The process of claim 1, wherein the debonder surfactant is present in an amount of 1 to 4 lbs per ton of fluff pulp fibers.

\* \* \* \* \*